United States Patent
Bartig et al.

[11] Patent Number: 5,871,529
[45] Date of Patent: Feb. 16, 1999

[54] ELECTRODE FOR HIGH IMPEDANCE HEART STIMULATION

[75] Inventors: Jeffrey T Bartig, St. Paul; Gary W Goebel, Vadnais Heights; Ronald W Heil, Jr., Roseville; Douglas A Heitkamp, White Bear Lake; Randall M Peterfeso, St. Paul, all of Minn.

[73] Assignee: Cardiac Pacemakers, Inc., St. Paul, Minn.

[21] Appl. No.: 783,958

[22] Filed: Jan. 16, 1997

[51] Int. Cl.⁶ ...................................................... A61N 1/05
[52] U.S. Cl. ............................................................ 607/122
[58] Field of Search .................................. 607/120–128; 128/642; 600/373–375

[56] References Cited

U.S. PATENT DOCUMENTS

| | | |
|---|---|---|
| 3,804,098 | 4/1974 | Friedman . |
| 4,030,508 | 6/1977 | Thalen ................................. 607/121 X |
| 4,559,951 | 12/1985 | Dahl et al. .............................. 128/642 |
| 4,633,880 | 1/1987 | Osypka et al. ........................... 128/642 |
| 4,649,937 | 3/1987 | DeHaan et al. . |
| 4,784,161 | 11/1988 | Skalsky et al. ...................... 607/122 X |
| 4,819,661 | 4/1989 | Heil, Jr. et al. . |
| 4,819,662 | 4/1989 | Heil, Jr. et al. . |
| 5,016,646 | 5/1991 | Gotthardt et al. . |
| 5,063,932 | 11/1991 | Dahl et al. .............................. 128/639 |
| 5,324,327 | 6/1994 | Cohen ..................................... 607/122 |
| 5,405,373 | 4/1995 | Petersson et al. ....................... 607/121 |
| 5,411,544 | 5/1995 | Mar et al. ............................... 607/122 |
| 5,545,205 | 8/1996 | Schulte et al. .......................... 607/123 |
| 5,554,178 | 9/1996 | Dahl et al. .............................. 607/122 |
| 5,578,068 | 11/1996 | Laske et al. ............................ 607/126 |

FOREIGN PATENT DOCUMENTS

| | | |
|---|---|---|
| 0057877 | 8/1982 | European Pat. Off. ............... 607/121 |
| 0573275 | 12/1993 | European Pat. Off. . |
| 612 538 | 8/1994 | European Pat. Off. ....................... 1/5 |
| 0620024 | 10/1994 | European Pat. Off. . |
| 2827595 | 5/1978 | Germany . |
| 2240721 | 8/1991 | United Kingdom . |

*Primary Examiner*—Jeffrey R. Jastrzab
*Attorney, Agent, or Firm*—Schwegman, Lundberg, Woessner & Kluth, P.A.

[57] ABSTRACT

An electrode adapted for implantation on or about the heart and for connection to a system for monitoring or stimulating cardiac activity includes an electrode tip which has one electrode at the far or distal end of the electrode tip. The distal end of the electrode further includes a screen capable of conducting electrical signals and pulses. An insulative masking member is positioned over a portion of the screen to define an electrical conducting surface. A conductor for carrying current is located within the electrode tip and is electrically connected to the conducting surface.

21 Claims, 2 Drawing Sheets

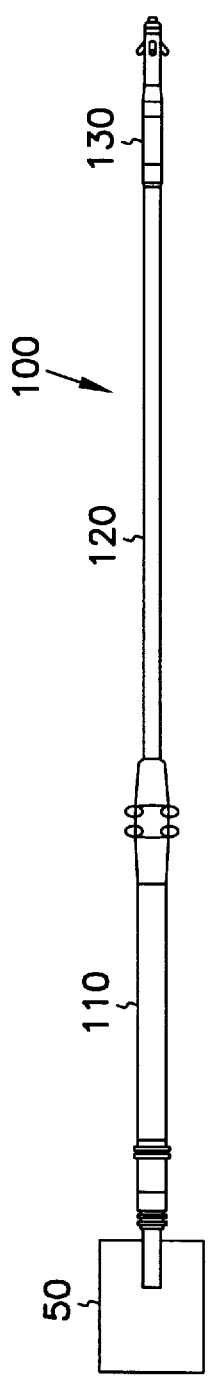
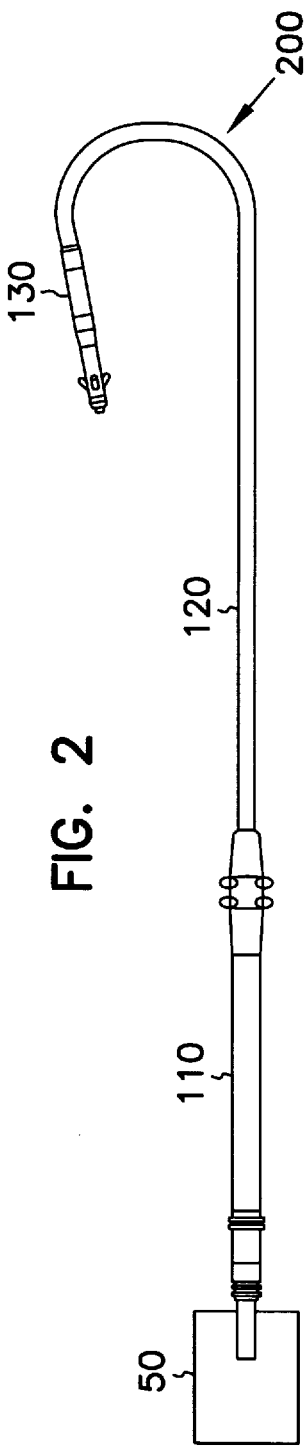

ELECTRODE FOR HIGH IMPEDANCE HEART STIMULATION

FIELD OF THE INVENTION

The present invention relates to the field of leads for pacing the heart. More particularly, this invention relates to an electrode tip for delivering electrical charges to the heart.

BACKGROUND OF THE INVENTION

Electrodes implanted in the body for electrical cardioversion or pacing of the heart are well known. More specifically, electrodes implanted in or about the heart have been used to reverse (i.e., defibrillate or cardiovert) certain life threatening arrhythmias, or to stimulate contraction (pacing) of the heart, where electrical energy is applied to the heart via the electrodes to return the heart to normal rhythm.

The sick sinus syndrome and symptomatic AV block constitute the major reasons for implantation of cardiac pacemakers today. Cardiac pacing may be performed by the transvenous method or by electrodes implanted directly onto the ventricular epicardium. Transvenous pacing may be temporary or permanent. In temporary transvenous pacing an electrode catheter is introduced into a peripheral vein and fluoroscopically positioned against the endocardium. Permanent transvenous pacing is performed under sterile surgical conditions. An electrode is positioned in the right ventricle or atrium through a subclavian vein, and the proximal terminals are attached to a pacemaker which is implanted subcutaneously.

Leads may be unipolar or bipolar. A unipolar lead system contains a single electrode in direct contact with the cardiac tissue which is connected to the negative terminal of the pacemaker with the second electrode positioned remotely, and usually consisting of the metallic pacemaker housing. In a bipolar lead system, the electrodes are in close proximity to each other and are situated within or on the heart.

In the past the surface areas of the tip electrodes have been relatively large. Typically, the electrodes have been at least equal in surface area to the cross section of the casing near the lead tip. In some applications, such as where patch type leads are used, the surface area of the electrode is much larger than the surface area associated with the diameter of the casing. In order to deliver an adequate charge to accomplish pacing of the heart, the entire surface area of the electrode must be charged to a certain level. Larger surface areas require larger amounts of energy. Energy is now an issue as the pulse generators are implanted subcutaneously within the patient. Health care costs are under constant downward pressure and insurance companies are trying to contain costs. Pacemaker replacement costs are less with a pulse generator having longer battery life since patients do not have to undergo operational procedures as often. Patients also benefit from longer battery lives, since a longer battery life means a longer time between hospital visits.

U.S. Pat. No. 5,405,373 discloses a distal end electrode having a tip with a surface which has a diameter equal to the diameter of the casing or base near the distal end electrode. In U.S. Pat. No. 5,405,373 the external surface of the electrode head is coated with a highly resistive insulating material, such as diamond-like carbon, which is deposited on the tip surface of the distal end electrode. The insulative layer is thin enough so that the threshold value is not affected. In other words, the coating or layer of insulating or dielectric material does not cause a standoff that would cause an increase in the pacing threshold. Depositing the layer of diamond-like carbon is both difficult and costly. This results in a pacing lead that is difficult and expensive to manufacture.

There is a need for a high impedance pacing lead that has a tip that is smaller in diameter than the casing near the electrode tip. Such an electrode tip would result in the use of less energy and increased battery life. There is also a need for a tip that accommodates eluting anti-inflammatory drugs. There is also a need for a pacing lead that maintains existing manufacturing techniques without adding an expensive process and new bio-materials into the human body.

SUMMARY OF THE INVENTION

An electrode adapted for implantation on or about the heart and for connection to a system for monitoring or stimulating cardiac activity includes a lead which has one electrode at the far or distal end of the lead. The distal end electrode has a base with a given diameter. The tip of the electrode has a diameter which is smaller than the base. A shoulder is formed between the base and the tip. The tip further includes an electrical conducting surface. An elastomeric insulative masking component is positioned over a portion of the electrical conducting surface. A conductor for carrying current is located within the lead and electrically connects the conducting surface and the pulse generator.

The elastomeric insulative masking component covers a portion of the electrical conducting surface of the distal tip electrode. The elastomeric insulative masking component creates a high impedance pathway for electrical signals carried to the heart. The insulative mask increases the local current density of the distal tip electrode and reduces the energy that needs to be delivered by the pacemaker to the heart. The end result is that the battery used to power the pulse generator lasts longer. Since the battery lasts longer, the pulse generator does not have to be replaced as often. This is beneficial to the patient since the pulse generator is implanted below the skin of the patient. Health care costs are reduced since the pulse generator does not have to be replaced as often in patients.

BRIEF DESCRIPTION OF THE DRAWINGS

FIG. 1 is a side view of a straight lead for monitoring and stimulating the heart.

FIG. 2 is a side view of a "J" lead for monitoring and stimulating the heart.

DESCRIPTION OF THE PREFERRED EMBODIMENT

Figure 3:
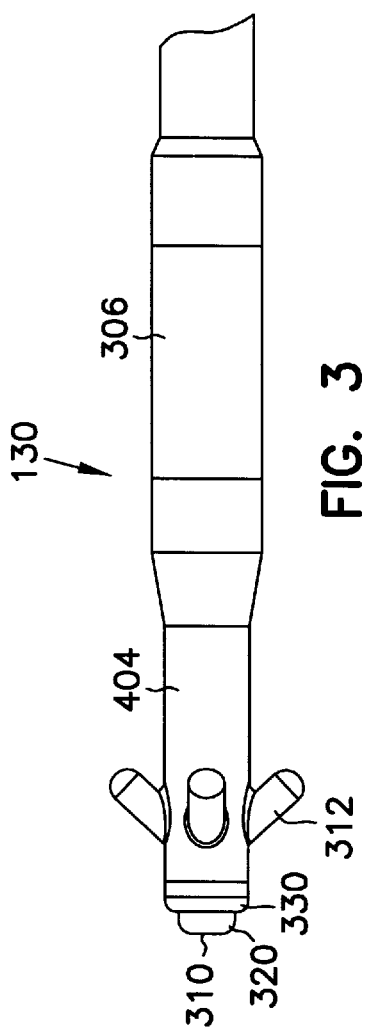
FIG.3 is a side view of the electrode tip of a lead for monitoring and stimulating the heart.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

FIG. 1 is a side view of a straight pacing lead 100. FIG. 2 is a side view of a "J" pacing lead 200. The "J" pacing lead 200 has the same basic components or parts as the straight pacing lead 100. The pacing lead 100 and the "J" pacing lead 200 are comprised of three portions, the connector terminal 110, the lead body 120 and the electrode end 130. Each of these portions of the pacing lead 100 will be discussed in the following paragraphs.

The connector terminal

It should be noted that there are numerous types of connector terminals which connect to a pulse generating unit 50. In the preferred embodiments shown in FIGS. 1 and 2, the connector terminal 110 is the same for both the straight pacing lead 100 and the "J" shaped lead 200. The lead terminal connector provides for the electrical connection between the lead and pulse generator 50. The connector terminal end 110 is designed to international IS-1 Standard ISO 5841-3(E). It should be noted that the tip can be used with any type of connector terminal end.

The lead body

The lead body 120 consists of electrical conductors which are covered by a biocompatible insulting material. The insulative material in this case is silicone rubber, polyurethane, or other insulative, flexible, biocompatible tubing material. There are numerous conductors within the lead body 120. The electrical conductors within the lead body 120 carry electrical energy to the heart. The electrical conductors also sense or pick up electrical signals from the heart. The electronics and software associated with the pulse generator use this signal from the heart to determine when to deliver the electrical energy or pace the heart.

It should be noted that the number of conductors within the lead body can be changed for particular applications. The conductors in each of the lead bodies 120 shown in FIGS. 1 and 2 include multifilar helical coils made of electrically conductive, corrosion-resistant material. FIG. 2 is a side view of a "J" pacing lead for electrically stimulating the heart. The "J" pacing lead is constructed in the same way as the straight lead. The "J" type lead is more commonly used to accomplish an implantation of the pacing lead into the right atrium of the heart.

The electrode tip

FIG. 3 is a side view of the electrode end 130 of a bipolar lead for electrically stimulating and monitoring the heart. The implantable electrode end 130 shown has a cylindrical body having one proximal electrode 306 and one distal electrode 310. Both the proximal 306 and distal 310 electrodes are made of electrically conductive, corrosion resistant material, and are of cylindrical configuration. This proximal electrode serves as the anode. There are many different types of proximal electrode configurations that are used for different lead applications. The base 303 (shown in FIG. 4) of the electrode end 130 is formed from a metal, such as titanium or an alloy of titanium which is electrically conductive but resistant to corrosion and suitable for implantation in the body. The base 303 (shown in FIG. 4) is covered with a biocompatible insulative material 404, such as silicone rubber tubing. The electrode end 130 also includes the distal electrode 310. The distal electrode includes a screen 320 and a masking component 330. The screen 320 is attached to the base 303 (see FIG. 4). The masking component 330 is positioned over the shoulder 332 and over a portion of the screen 320. A set of tines 312 is attached to the insulative tubing material 404. Tines 312 are used for passive fixation of the distal electrode 310 in the desired location proximate to the heart tissue. The tines 312 are designed to engage cardiac structures within the right ventricle or right atrium to provide acute and chronic anchoring of the electrode. The molded rubber tine neck component is bonded to the conductor coil insulation tubing 404 and the electrode tip body. The tines are located between the proximal and distal electrodes. Although tines 312 (see FIG. 3) are shown, it is contemplated that other forms of fixation, such as a helix for active fixation into the heart could also be used to anchor the electrode.

The mask component 330 is made of an insulative elastomeric material. Silicone rubber tubing is a biocompatible material used to make the mask component 330. The screen 320 is of a porous construction. A screen is made of electrically conductive, corrosion resistant material. Using a screen 320 having a porous construction allows for fibrotic in growth. This provides for a further anchoring of the distal end 130 and also increases the sensing capability of the distal electrode 310. The sensing capability is enhanced because the porous screen 320 has more surface area than a corresponding flat piece of material. The ingrowth of fibrotic tissue into the screen 320 provides contact with the increased amount of surface. As can be seen from FIG. 3, the screen 320 which makes up the distal electrode 310 has a diameter which is smaller than the outside diameter of the cylindrical body or base 303 of the electrode end 130. The outside diameter of the cylindrical body or base 303 is of a diameter believed to be sufficient so as not to perforate the heart wall. At the junction of the screen 320 and the base 303, a shoulder 332 is formed. The shoulder limits the depth to which the distal electrode 310 penetrates the endocardium or heart muscle. The screen 320 is shaped somewhat like a hat in that it has a rim and a convex portion. The rim of the screen 320 abuts the shoulder 332.

Figure 4:
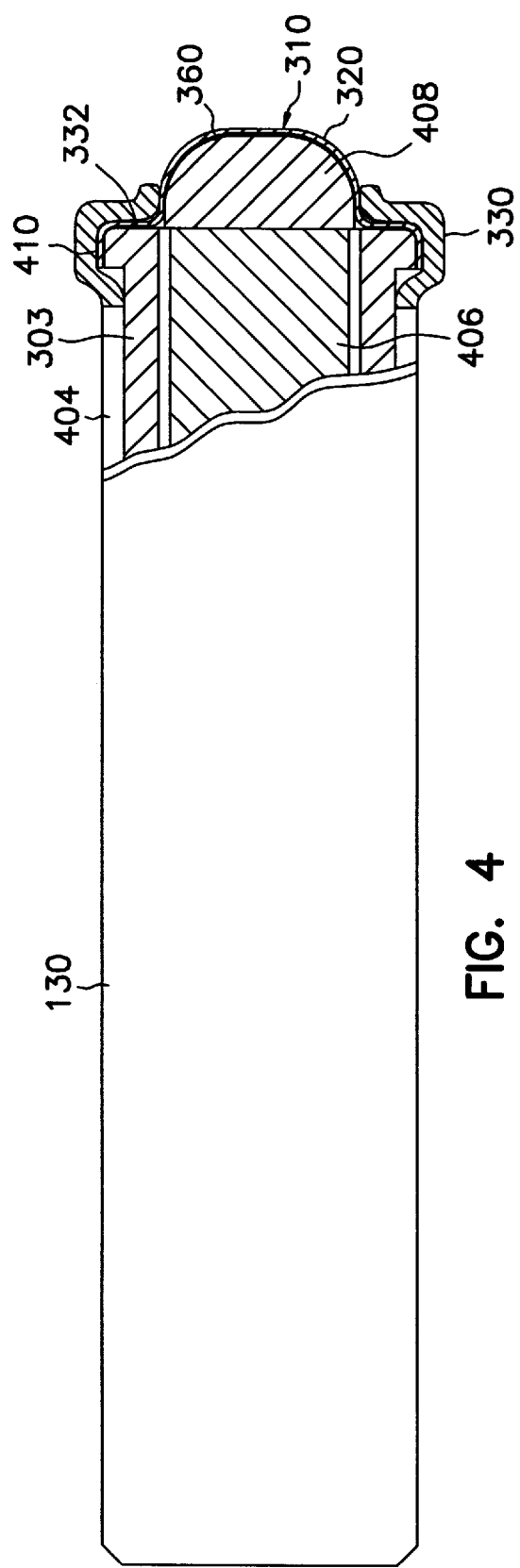
FIG. 4 is a partial, cut-away, cross-sectional view of the electrode tip of a lead for monitoring and stimulating the heart.

FIG. 4 shows a partial cross-sectional view of the electrode end 130. The distal portion of the electrode end 130 is provided with a central bore 406. Contained within this central bore 406 is a silicone steroid matrix which elutes steroid to decrease inflammation. The internalized silicone matrix containing a steroid is one method for delivering steroid to an area around the distal electrode 310. There are other methods and apparatus that can be employed to deliver steroid to the tissue surrounding the distal electrode 310, such as an external steroid matrix that forms a ring around the lead body near the electrode end 130. It is also contemplated that this invention may be used for any of a number of different applications and that in some instances it may be unnecessary to use a steroid or drug delivery system.

A multifilar conductor coil within the lead body 120 electrically contacts the base 303 and the screen 320. More specifically, electrical contact is made between the helical coil conductors and the portion of the screen uncovered by the masking component 330, now referred to as electrical contact surface 360. The surface of screen 320 of the distal electrode 310 is of porous construction and has a nominal pacing surface area in the range of 1.7–2.6 mm$^2$. It has been found that a nominal pacing area of about 2.0 mm$^2$ provides a contact surface with adequate sensing and high enough impedance.

The size or area of the contact surface 360 is selected so as to optimize several competing design factors. The area of the contact surface 360 has to be large enough so that the electrode can adequately sense the electrical signals of the heart. The area of the contact surface also has to be small enough so that a high impedance is produced to minimize the energy necessary to pace the heart.

The distal portion of the central bore 406 also includes a ball 408 of wound electrically conductive, corrosion-resistant material that is commonly referred to as a mesh ball. The mesh ball 408 sits inside the screen 320 within the central bore 406. The function of the mesh ball is to increase the sensing surface area of the distal electrode 310 without increasing the pacing surface area. Both the pacing and the sensing surface areas are important parameters of the lead system. The pacing surface area is determined by the exposed screen 320 of the distal electrode 310. The sensing surface area is determined by the exposed electrical surfaces both external and internal to the porous tip of the distal electrode 310. The sensing capability is enhanced by the mesh ball 408 since it tends to act like foil on a TV antennae. It should be noted that the mesh ball 408 is not necessarily needed to practice this invention. It does provide some added benefits, as listed above, and also helps the screen 320 maintain its shape.

The electrical contact surface 360 of the distal electrode 310 is defined by the addition of a masking component 330 applied to the base 303 and over the screen, 320. The masking component 330 is a short length of silicone rubber tubing which stretches over the end of the distal electrode 310 and covers a portion of the screen 320. The masking component 330 also stretches over the shoulder 332 on base 303. The size or area of the electrical contact surface 360 is defined by the amount of silicone tubing used to mask the screen 320. If less area is desired for the electrical contact surface 360, a longer masking component 330 is used. The nominal surface area of the electrical contact surface is 2.0 mm². The masking component 330 is held in place primarily by a compressive force which occurs after the elastomeric material is stretched over the base 303 and a portion of the screen 320. A medical adhesive 410 provides a secondary holding force between the base 303, the screen 320, and the masking component 330.

An additional advantage of using silicone rubber tubing for the masking component 330, is that this material has been implanted within humans previously and the characteristics of that material in that environment are well known. The use of a masking component 330 is less dependent on a new technology, which makes the solution much more economical than other solutions. The open window of electrically active mesh will make tissue contact in vivo and determine the pacing impedance of the lead.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A distal tip electrode adapted for implantation on or about the heart and for connection to a system for monitoring or stimulating cardiac activity, said electrode comprising:
   an electrically conductive base having a first diameter;
   an electrode tip attached to said base and having a second diameter less than the first diameter;
   a surface at the distal end of the electrode tip, said surface further comprising an electrical conducting surface; and
   a high impedance masking member positioned over a portion of said electrical conducting surface, said masking member reducing the surface area of the electrical conducting surface in contact with the heart.

2. The distal end electrode of claim 1 wherein the masking component is made of silicone rubber polymer.

3. The distal end electrode of claim 1 further comprising a shoulder formed at the juncture of the base and tip.

4. A distal tip electrode adapted for implantation on or about the heart and for connection to a system for monitoring or stimulating cardiac activity, said electrode comprising:
   a base having a first diameter;
   an electrode tip attached to said base and having a second diameter less than the first diameter;
   a surface at the distal end of the electrode tip, said surface further comprising an electrical conducting surface; and
   a high impedance masking member positioned over a portion of said electrical conducting surface, wherein the masking member is made of silicone tubing.

5. The distal end electrode of claim 4 further comprising tines positioned near the distal end electrode, said tines for attaching to the inner wall of the heart.

6. A distal tip electrode adapted for implantation on or about the heart and for connection to a system for monitoring or stimulating cardiac activity, said electrode comprising:
   a base having a first diameter;
   an electrode tip attached to said base and having a second diameter less than the first diameter;
   a surface at the distal end of the electrode tip, said surface further comprising an electrical conducting surface; and
   a high impedance masking member positioned over a portion of said electrical conducting surface, wherein the electrical conducting surface includes a porous screen.

7. The distal end electrode of claim 6 wherein the masking component covers a portion of the screen to define the electrical conducting surface.

8. The distal end electrode of claim 7 wherein the electrode tip has a bore within the tip, said electrode further comprising a drug-containing matrix within said bore.

9. The distal end electrode of claim 8 wherein the drug-containing matrix elutes an anti-inflammatory agent through the porous screen.

10. The distal end electrode of claim 7 wherein the electrode tip has a bore within the tip, said electrode comprising an electrically conductive, corrosion-resistant mesh ball.

11. The distal end electrode of claim 10 wherein the drug-containing matrix elutes an anti-inflammatory agent through the porous screen and the mesh ball.

12. The distal end electrode of claim 6 wherein the masking component covers a portion of the screen to define the electrical conducting surface that is nominally 2.0 mm² in size.

13. The distal end electrode of claim 12 wherein the electrode tip has a bore within the tip, said electrode further comprising a drug-containing matrix within said bore.

14. The distal end electrode of claim 12 wherein the electrode tip has a bore within the tip, said electrode comprising an electrically conductive, corrosion-resistant mesh ball.

15. A lead adapted for implantation on or about the heart and for connection to a system for monitoring or stimulating cardiac activity, said lead comprising:
   a lead body including an electrode tip;
   a surface at the distal end of the electrode tip, said surface further comprising:

an electrical conducting surface; and a masking member positioned over a portion of said electrical conducting surface to produce a substantially annular, unmasked conductive surface; and an electrical conductor associated with the lead body and electrically connecting with the electrical conducting surface.

16. The lead of claim 15 wherein the electrical conducting surface is a screen.

17. A lead adapted for implantation on or about the heart and for connection to a system for monitoring or stimulating cardiac activity, said lead comprising:

a lead body having a diameter, said lead body including an electrode tip having a generally cylindrical main body;

a surface at the distal end of the electrode tip, said surface further comprising:
an electrical conducting surface; and
a masking member positioned over a portion of said electrical conducting surface;

an electrical conductor associated with the lead body and electrically connecting with the electrical conducting surface;

a rim having an outer diameter about the same as the lead body diameter; and a convex portion extending away from the generally cylindrical main body of the electrode tip, said convex portion within the rim of the electrical conducting surface.

18. The lead of claim 17 wherein the masking member is positioned over the rim of the electrical conducting surface, said masking member made of an electrical insulation material.

19. The lead of claim 18 wherein the masking member is positioned over the rim of the electrical conducting surface and over a portion of the convex portion of the electrical conducting surface.

20. The lead of claim 18 wherein the electrode tip has an opening therein, said electrode tip further comprising a matrix containing a drug which fits within the opening.

21. The lead of claim 20 further comprising a mesh ball of corrosion-resistant, electrically conductive material positioned between the convex portion of the electrical conducting surface and the matrix containing a drug, said matrix containing a drug eluting a drug through the mesh ball and through the electrical conducting surface.

* * * * *